US00PP19479P2

(12) United States Plant Patent
Hooijman

(10) Patent No.: US PP19,479 P2
(45) Date of Patent: Nov. 25, 2008

(54) ***GYPSOPHILA* PLANT NAMED 'ESM ALICIA'**

(50) Latin Name: *Gypsophila hybrida*
Varietal Denomination: Esm Alicia

(75) Inventor: Aloysius A. J. Hooijman, Aalsmeer (NL)

(73) Assignee: ESmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 11/903,795

(22) Filed: Sep. 25, 2007

(51) Int. Cl.
*A01H 5/00* (2006.01)

(52) U.S. Cl. ..... Plt./354
(58) Field of Classification Search ..... Plt./354
See application file for complete search history.

(56) References Cited

PUBLICATIONS

UPOV–ROM GTITM, Plant Variety Database, Apr. 2007, GTI Jouve Retrieval Software, Citation for gypsophila 'Esm Alicia'.*

* cited by examiner

*Primary Examiner*—Annette H Para
*Assistant Examiner*—S. B. McCormick-Ewoldt
(74) *Attorney, Agent, or Firm*—C. A. Whealy

(57) ABSTRACT

A new and distinct cultivar of *Gypsophila* plant named 'Esm Alicia', characterized by its erect and strong flowering stems; early, uniform and freely flowering habit; semi-double luminous white-colored flowers; and good postproduction longevity.

2 Drawing Sheets

Botanical designation: *Gypsophila hybrida.*
Cultivar denomination: 'Esm Alicia'.

BACKGROUND OF THE INVENTION

The present invention relates to a new and distinct cultivar of *Gypsophila* plant, botanically known as *Gypsophila hybrida,* grown commercially as a cut flower, and hereinafter referred to by the name 'Esm Alicia'.

The new *Gypsophila* is a product of a planned breeding program conducted by the Inventor in El Quinche, Pichincha, Ecuador. The objective of the breeding program is to create new freely flowering *Gypsophila* cultivars with many petals per flower and straight stems.

The new *Gypsophila* originated from a cross-pollination made by the Inventor in El Quinche, Pichincha, Ecuador in February, 2003 of a proprietary selection of *Gypsophila hybrida* identified as Line 146, not patented, as the female, or seed, parent with a proprietary selection of *Gypsophila hybrida* identified as Line 31, not patented, as the male, or pollen, parent. The cultivar Esm Alicia was discovered and selected by the Inventor as a flowering plant from within the progeny of the stated cross-pollination in a controlled environment in El Quinche, Pichincha, Ecuador.

Asexual reproduction of the new *Gypsophila* by cuttings in a controlled environment in El Quinche, Pichincha, Ecuador since December, 2003, has shown that the unique features of this new *Gypsophila* are stable and reproduced true to type in successive generations.

SUMMARY OF THE INVENTION

The cultivar Esm Alicia has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Esm Alicia'. These characteristics in combination distinguish 'Esm Alicia' as a new and distinct cultivar of *Gypsophila:*

1. Erect and strong flowering stems.
2. Early, uniform and freely flowering habit.
3. Semi-double luminous white-colored flowers.
4. Good postproduction longevity.

In side-by-side comparisons conducted in El Quinche, Pichincha, Ecuador, plants of the new *Gypsophila* differed from plants of the female parent selection in the following characteristics:

1. Plants of the new *Gypsophila* had stronger flowering stems than plants of the female parent selection.
2. Plants of the new *Gypsophila* had larger flowers than plants of the female parent selection.

In side-by-side comparisons conducted in El Quinche, Pichincha, Ecuador, plants of the new *Gypsophila* differed from plants of the male parent selection in the following characteristics:

1. Plants of the new *Gypsophila* were taller than plants of the male parent selection.
2. Plants of the new *Gypsophila* were more freely flowering than plants of the male parent selection.

Plants of the new *Gypsophila* can be compared to plants of the *Gypsophila* cultivar Esm Cold, disclosed in a U.S. Plant Patent application filed concurrently. In side-by-side comparisons conducted in El Quinche, Pichincha, Ecuador, plants of the new *Gypsophila* differed from plants of the cultivar Esm Cold in the following characteristics:

1. Plants of the new *Gypsophila* were taller than plants of the cultivar Esm Cold.
2. Plants of the new *Gypsophila* had longer internodes than plants of the cultivar Esm Cold.

3. Flower petals of plants of the new *Gypsophila* were more luminous white in color as flower petals of plants of the cultivar Esm Cold.

Plants of the new *Gypsophila* can also be compared to plants of the *Gypsophila* cultivar Dangypflash, disclosed in U.S. Plant Pat. No. 12,422. In side-by-side comparisons conducted in El Quinche, Pichincha, Ecuador, plants of the new *Gypsophila* differed from plants of the cultivar Dangypflash in the following characteristics:

1. Plants of the new *Gypsophila* were taller and more narrow than plants of the cultivar Dangypflash.
2. Plants of the new *Gypsophila* had longer internodes than plants of the cultivar Dangypflash.
3. Plants of the new *Gypsophila* had shorter leaves than plants of the cultivar Dangypflash.
4. Inflorescences of plants of the new *Gypsophila* were longer lasting than inflorescences of plants of the cultivar Dangypflash.

BRIEF DESCRIPTION OF THE PHOTOGRAPHS

The accompanying photographs illustrate the overall appearance of the new *Gypsophila*. These photographs show the colors as true as it is reasonably possible to obtain in colored reproductions of this type. Colors in the photographs may differ slightly from the color values cited in the detailed botanical description which accurately describe the colors of the new *Gypsophila*.

The photograph on the first sheet comprises a side perspective view of a typical flowering stem of 'Esm Alicia'.

The photograph on the second sheet is a close-up view of typical flowers of 'Esm Alicia'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in El Quinche, Pichincha, Ecuador during the winter in ground beds in an outdoor nursery and under conditions and practices which approximate those generally used in commercial cut *Gypsophila* production. During the production of the plants, day temperatures ranged from 12° C. to 30° C. and night temperatures ranged from 7° C. to 11° C. Plants were pinched one time about five weeks after planting and were grown under long day/short day conditions. Measurements and numerical values represent averages for typical six-month old flowering plants.

Botanical classification: *Gypsophila hybrida* cultivar Esm Alicia.

Commercial classification: Cut flower *Gypsophila*.

Parentage:

*Female, or seed, parent.*—Proprietary selection of *Gypsophila hybrida* identified as Line 146, not patented.

*Male, or pollen, parent.*—Proprietary selection of *Gypsophila hybrida* identified as Line 31, not patented.

Propagation:

*Type.*—By cuttings.

*Time to initiate roots.*—About 16 to 21 days at 17° C. to 25° C.

*Time to produce a rooted cutting.*—About five to six weeks at 17° C. to 25° C.

*Root description.*—Fine; 163in color.

*Rooting habit.*—Freely branching.

Plant description:

*Appearance.*—Perennial cut flower. Erect and strong flowering stems; inverted triangle form. Freely flowering; many-petalled luminous white-colored flowers arranged in symmetrical and moderately dense compound cymes. Vigorous growth habit.

*Branching habit.*—After pinching, about 19 flowering stems develop per year.

*Plant height.*—About 110 cm.

*Plant diameter or spread.*—About 70 cm.

*Flowering stems.*—Length: About 105 cm. Diameter: About 5 mm. Internode length: About 8.6 cm. Strength: Strong. Texture: Glabrescent. Color: 138B.

Foliage description:

*Arrangement.*—Opposite, decussate, simple; sessile.

*Length.*—About 6.4 cm.

*Width.*—About 1.6 cm.

*Shape.*—Lanceolate.

*Apex.*—Acute.

*Base.*—Cuneate.

*Margin.*—Entire.

*Texture, upper and lower surfaces.*—Smooth, glabrous; waxy.

*Venation pattern.*—Parallel.

*Color.*—Developing foliage, upper surface: 139A. Developing foliage, lower surface: 147A. Fully expanded foliage, upper surface: Between 139A and 147A; venation, 137A. Fully expanded foliage, lower surface: 139A; venation, 137B.

Flower description:

*Flower arrangement and habit.*—Symmetrical compound cymes with numerous many-petalled luminous white-colored flowers, flowers rotate. Very freely flowering, about 1,500 flowers per inflorescence. Flowers face mostly upright.

*Flowering response.*—In Ecuador, plants flower year round. Plants begin flowering about 14 weeks after planting.

*Post-production longevity.*—As a cut flower, flowers last for about twelve days. Flowers persistent.

*Fragrance.*—Slightly fragrant; pleasant.

*Inflorescence height.*—About 105 cm.

*Inflorescence diameter.*—About 50 cm.

*Flower diameter.*—About 1.2 cm.

*Flower depth (height).*—About 6 mm.

*Flower buds.*—Length: About 3 mm. Diameter: About 3 mm. Shape: Nearly globose. Color: 143A.

*Petals/petaloids.*—Quantity per flower: About 50 arranged in clusters. Length: About 5 mm. Width: About 2 mm. Shape: Oval to spatulate. Apex: Truncate, emarginate or obtuse. Margin: Entire. Texture, upper and lower surfaces: Smooth, glabrous; waxy. Color: When opening and fully opening, upper surface: Close to N155D; towards the base, close to 144A; color becoming closer to 155A with development. When opening and fully opening, lower surface: Close to N155D.

*Sepals.*—Quantity per flower: About five to seven fused to form a cup-shaped calyx. Length: About 3.5 mm. Width: About 2.4 mm. Shape: Roughly linear. Apex: Acute. Margin: Entire. Texture, upper and lower surfaces: Smooth, glabrous. Color: When developing, upper surface: 137C. When developing, lower surface: 137B. Fully developed, upper surface: 137A. Fully developed, lower surface: 138A.

*Peduncles.*—Length: About 7 cm. Diameter: About 4 mm. Strength: Strong. Angle: About 39° from vertical. Texture: Smooth, glabrous. Color: 146C.

*Pedicels.*—Length: About 6.5 mm. Diameter: About 0.5 mm. Strength: Strong. Angle: About 60° from vertical. Texture: Smooth, glabrous. Color: 137B.

*Reproductive organs.*—Stamens: Quantity per flower: Eight. Anther shape: Reniform to globose. Anther length: Less than 1 mm. Anther color: 160C. Pollen amount: Scarce. Pollen color: Close to 160C. Pistils: Quantity per flower: One. Pistil length: About 5.5 mm. Style length: About 4.2 mm. Style color: Close to N155D. Stigma shape: Curved apiculate. Stigma color: Close to N155D. Ovary color: 143C; occasionally towards the apex, 165A. Seed/fruit: Seed and fruit production has not been observed.

Disease/pest resistance: Plants of the new *Gypsophila* have not been shown to be resistant to pathogens and pests common to *Gypsophila*.

Temperature tolerance: Plants of the new *Gypsophila* have been observed to tolerate temperatures ranging from about 7° C. to about 30° C.

It is claimed:

1. A new and distinct *Gypsophila* plant named 'Esm Alicia' as illustrated and described.

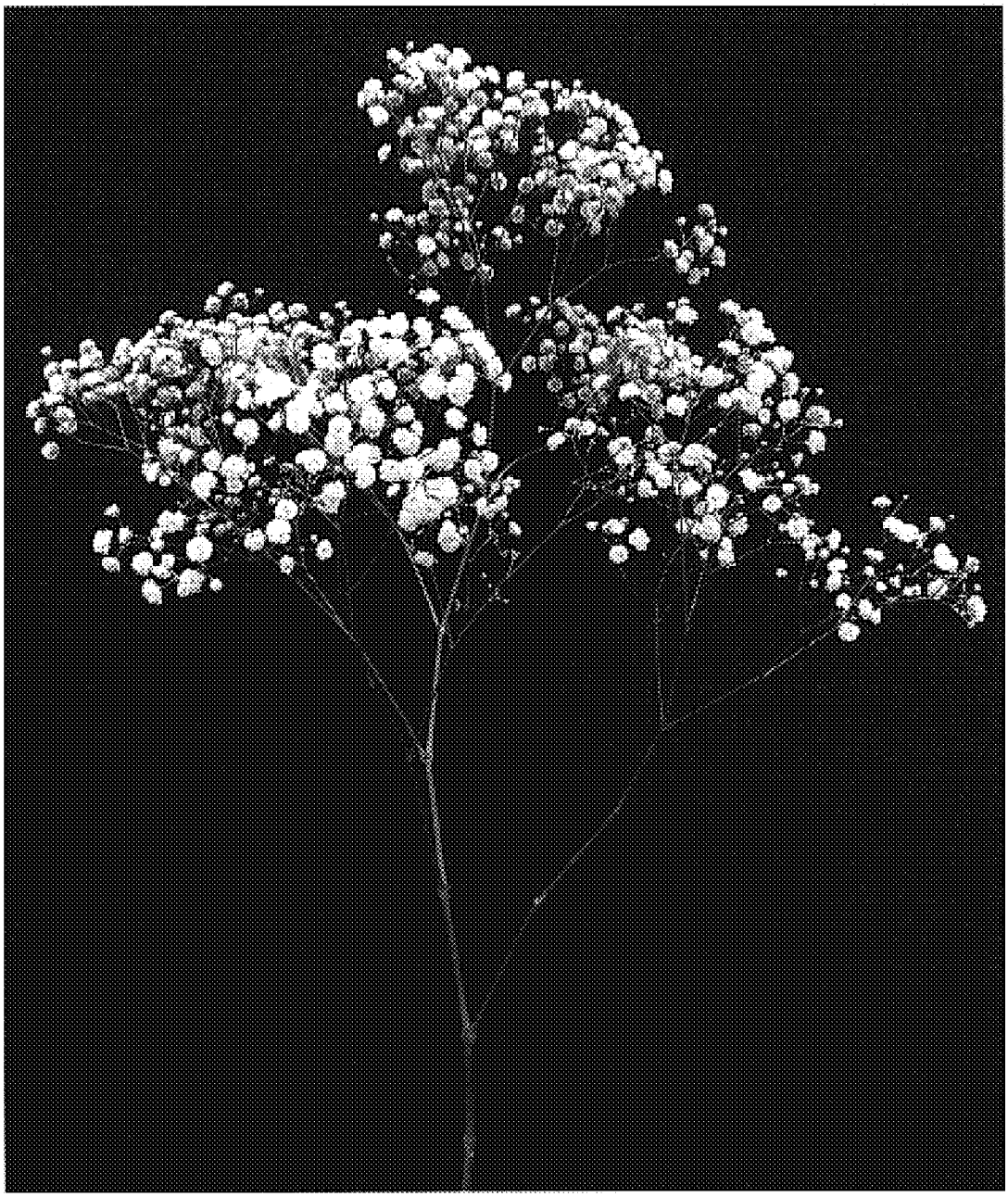

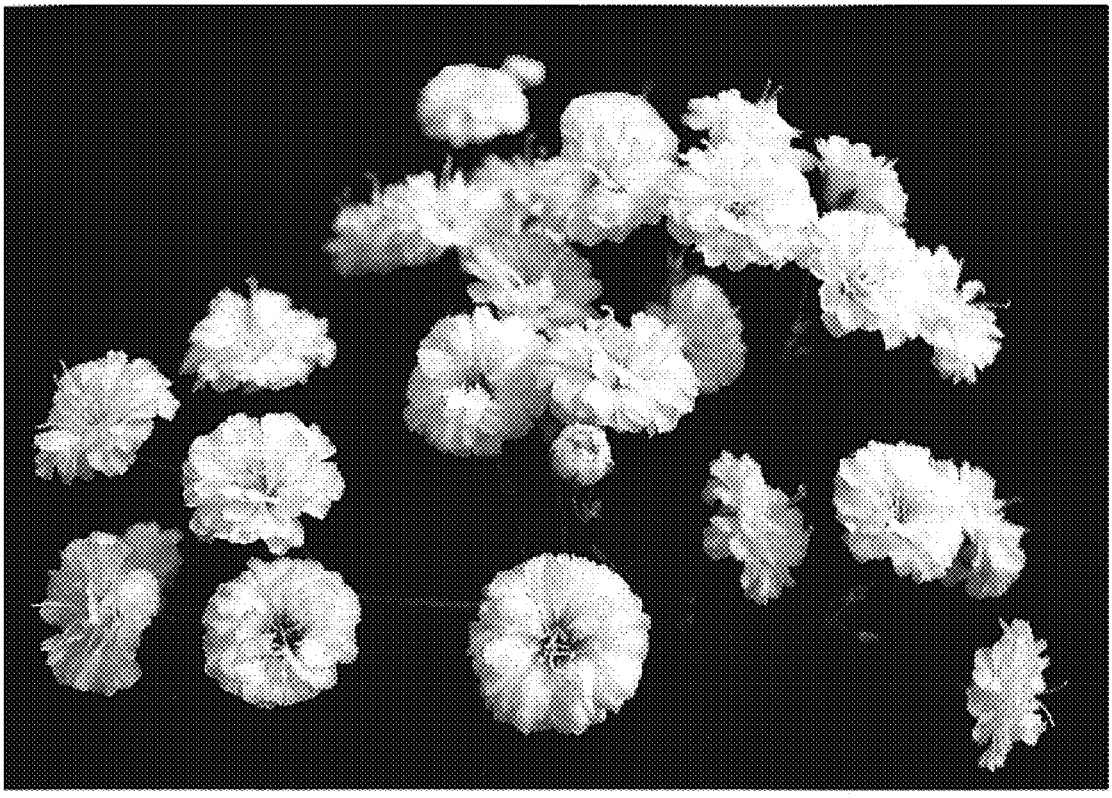

* * * * *